(12) United States Patent
Srinivasan et al.

(10) Patent No.: US 7,390,386 B2
(45) Date of Patent: Jun. 24, 2008

(54) AQUEOUS STREAM PURIFIER AND METHOD OF USE

(75) Inventors: Kannan Srinivasan, Sunnyvale, CA (US); Nebojsa Avdalovic, Cupertino, CA (US)

(73) Assignee: Dionez Corporation, Sunnyvale, CA (US)

( * ) Notice: Subject to any disclaimer, the term of this patent is extended or adjusted under 35 U.S.C. 154(b) by 434 days.

(21) Appl. No.: 10/308,865

(22) Filed: Dec. 2, 2002

(65) Prior Publication Data

US 2003/0132163 A1 Jul. 17, 2003

Related U.S. Application Data

(63) Continuation-in-part of application No. 10/043,645, filed on Jan. 10, 2002.

(51) Int. Cl.
*B01D 15/08* (2006.01)

(52) U.S. Cl. .................. 204/524; 204/531; 204/533; 204/536

(58) Field of Classification Search ............... 204/524, 204/531, 533, 536
See application file for complete search history.

(56) References Cited

U.S. PATENT DOCUMENTS

| | | | | |
|---|---|---|---|---|
| 4,057,483 A | * | 11/1977 | Giuffrida | ............... 204/630 |
| 4,334,949 A | | 6/1982 | Ameen et al. | |
| 5,045,204 A | | 9/1991 | Dasgupta | |
| 5,352,360 A | | 10/1994 | Stillian et al. | |
| 5,597,481 A | | 1/1997 | Stillian et al. | |
| 5,597,734 A | | 1/1997 | Small et al. | |
| 5,633,171 A | | 5/1997 | Small et al. | |
| 5,773,615 A | * | 6/1998 | Small et al. | ............... 436/161 |
| 6,027,643 A | | 2/2000 | Small et al. | |
| 6,036,921 A | | 3/2000 | Small et al. | |
| 6,077,434 A | * | 6/2000 | Srinivasan et al. | ............ 210/635 |
| 6,093,327 A | * | 7/2000 | Anderson et al. | ............ 210/660 |
| 6,225,129 B1 | | 5/2001 | Liu et al. | |
| 6,316,270 B1 | | 11/2001 | Small et al. | |
| 6,402,917 B1 | * | 6/2002 | Emery et al. | ............... 204/524 |
| 6,468,804 B1 | | 10/2002 | Anderson | |
| 2002/0011096 A1 | | 1/2002 | Johnson | |

FOREIGN PATENT DOCUMENTS

| | | |
|---|---|---|
| EP | 1 074 837 | 2/2001 |
| EP | 1110914 A2 | 6/2001 |
| FR | 2684093 A1 | 5/1993 |

OTHER PUBLICATIONS

DIONEX Corporation, "Installation Instructions and Trouble Shooting Guide for the IonPac® ATC Anion Trap Column" Dec. 1998, pp. 4, 5.

* cited by examiner

*Primary Examiner*—Arun S. Phasge
(74) *Attorney, Agent, or Firm*—Morgan, Lewis & Bockius LLP; David J. Brezner

(57) ABSTRACT

An electrolytic method is provided for purifying an aqueous stream, including at least one contaminant ion. In one embodiment, the eluent stream flows through a purifying flow channel, including ion exchange bed, an electric field is applied through the flowing eluent stream in the purifying flow channel, and the contaminant ion is removed from the eluent stream. In another embodiment, no electric field is applied and the ion exchange bed is periodically regenerated. Two beds may be used with one bed on line while the other bed is regenerated followed by a reversal of flow.

21 Claims, 11 Drawing Sheets

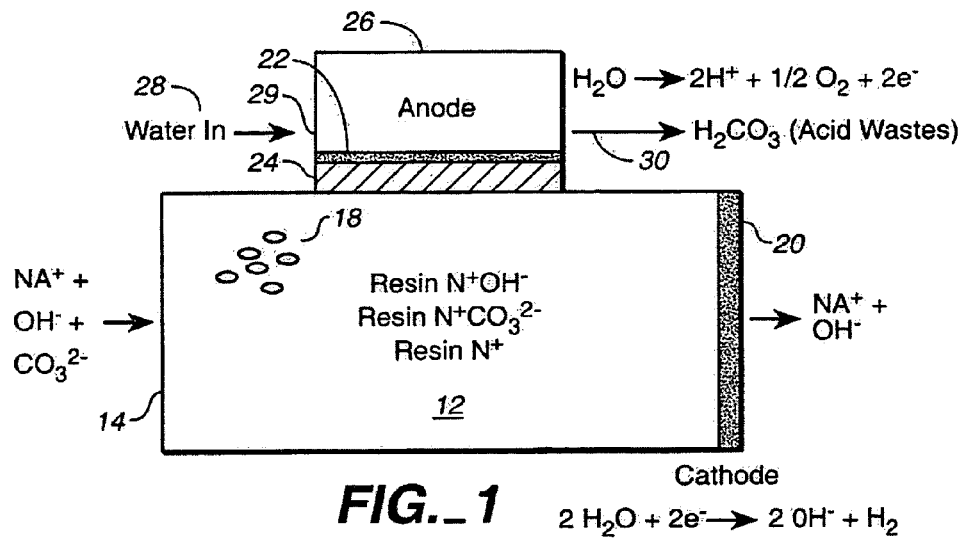
FIG._1
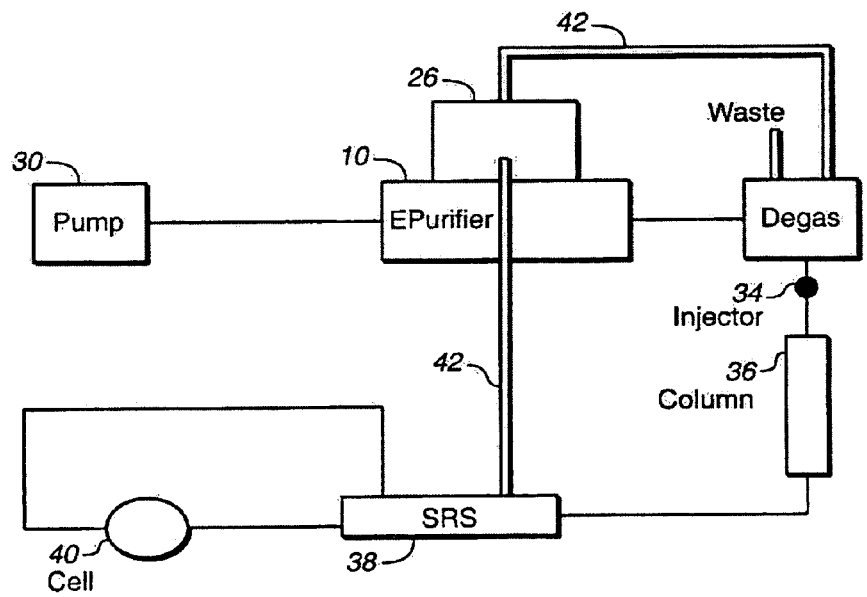
FIG._2

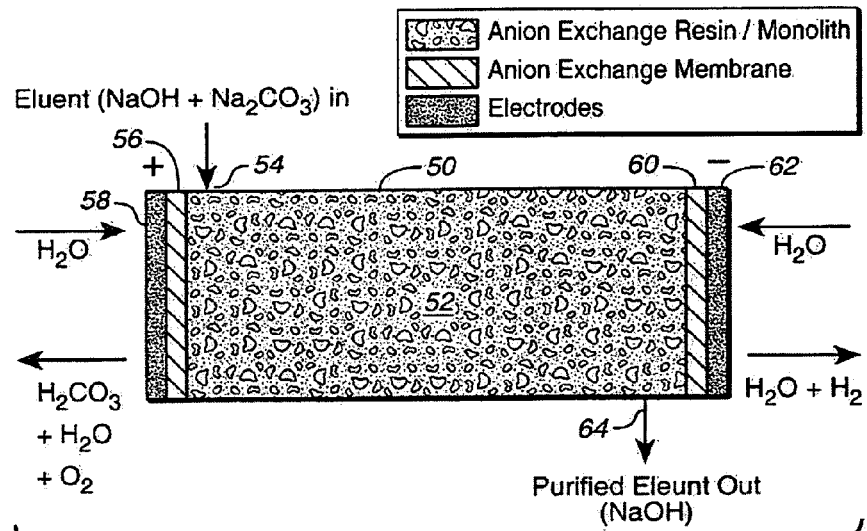
*FIG._3*
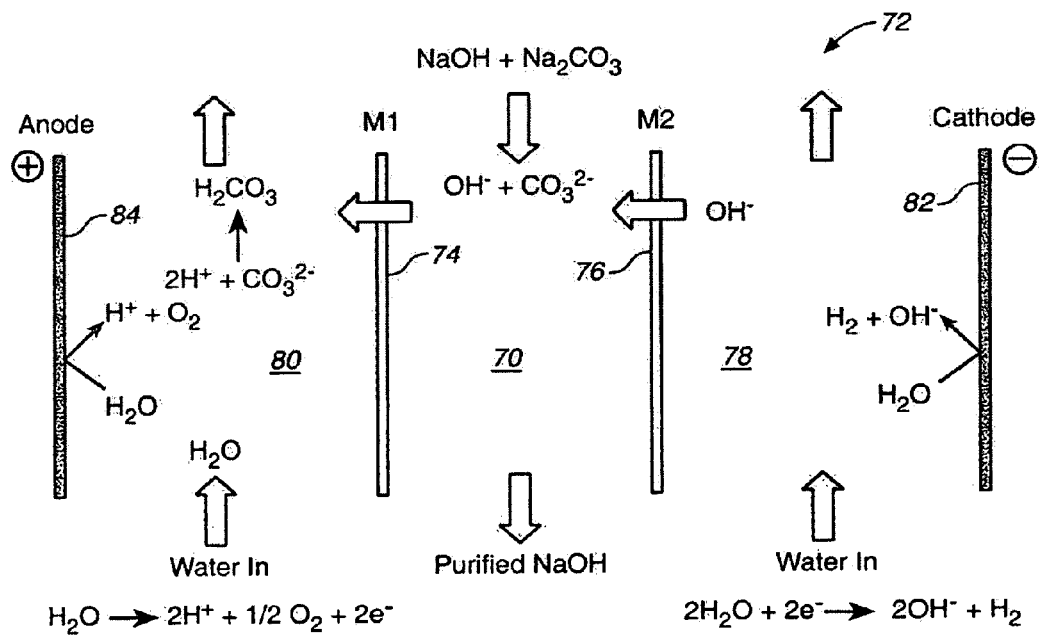
*FIG._4*

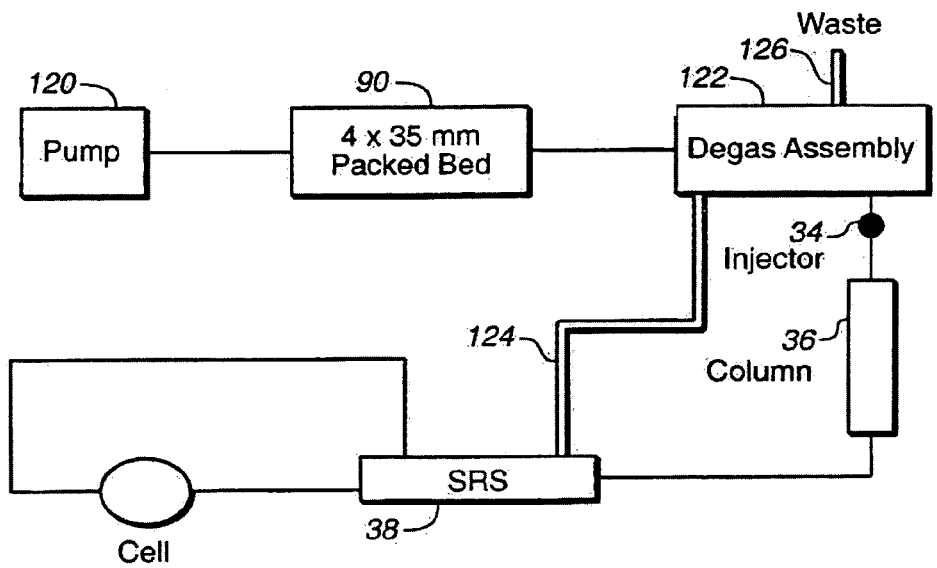
FIG._7
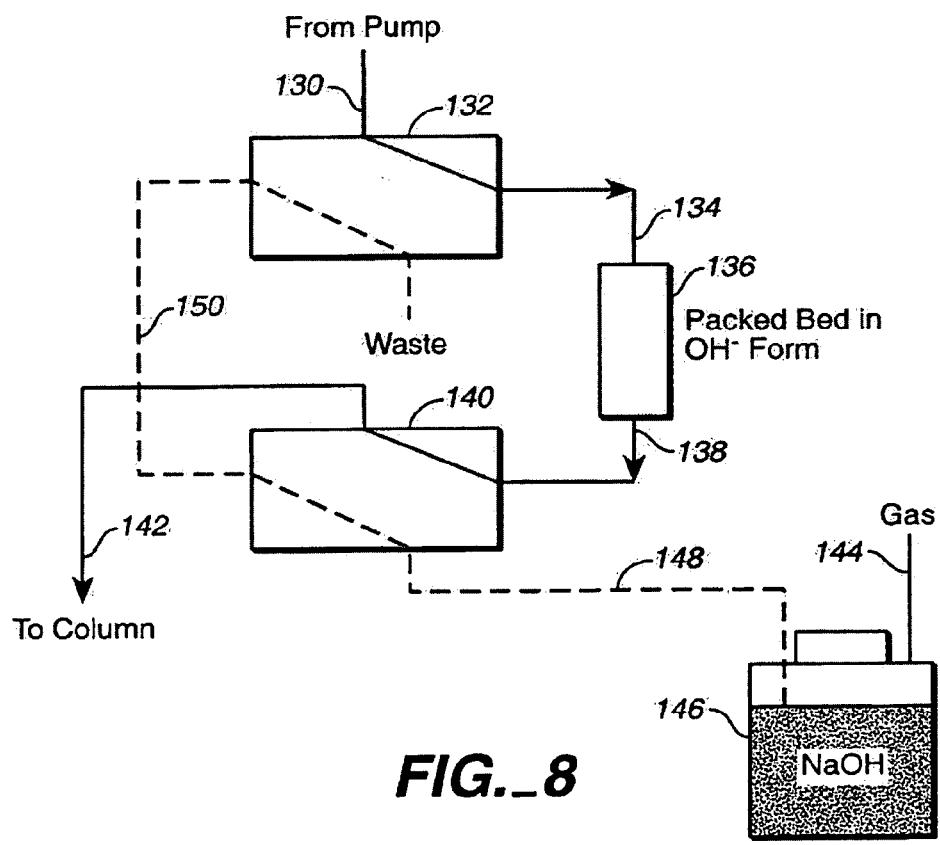
FIG._8

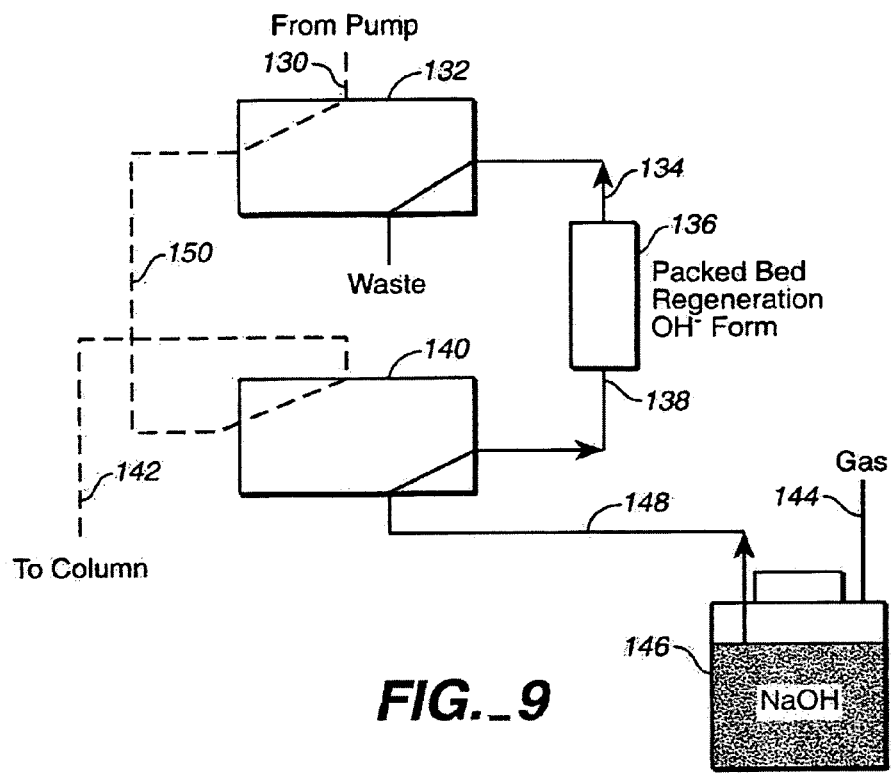
FIG._9
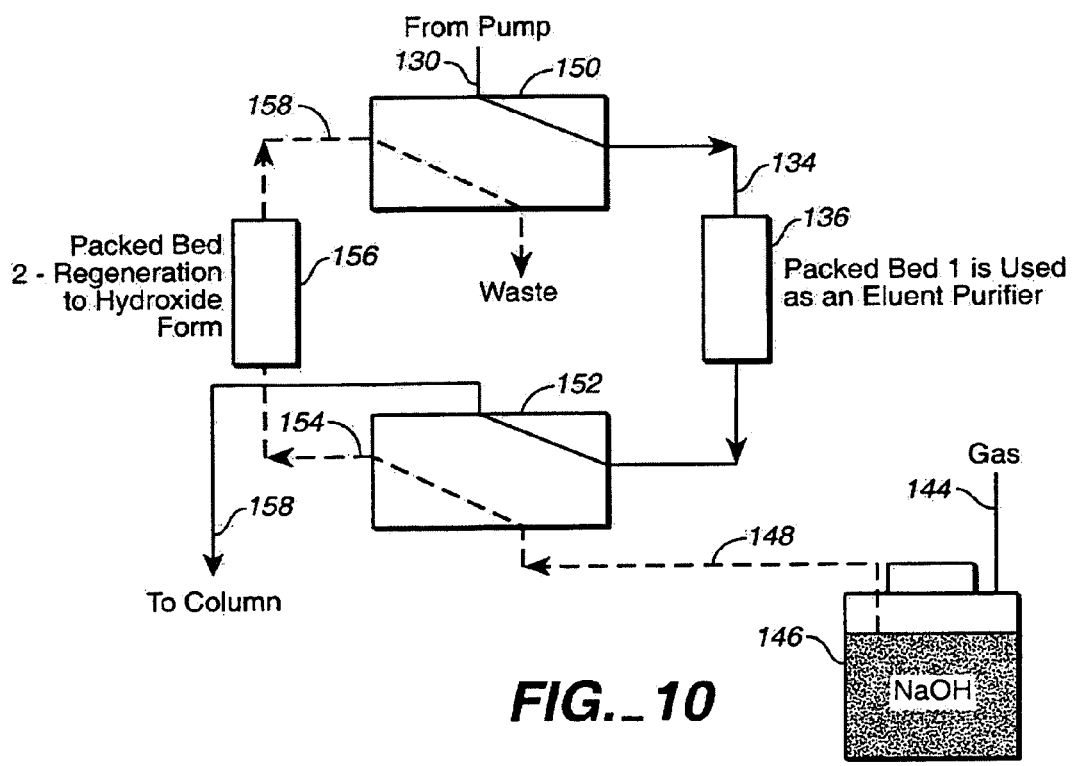
FIG._10

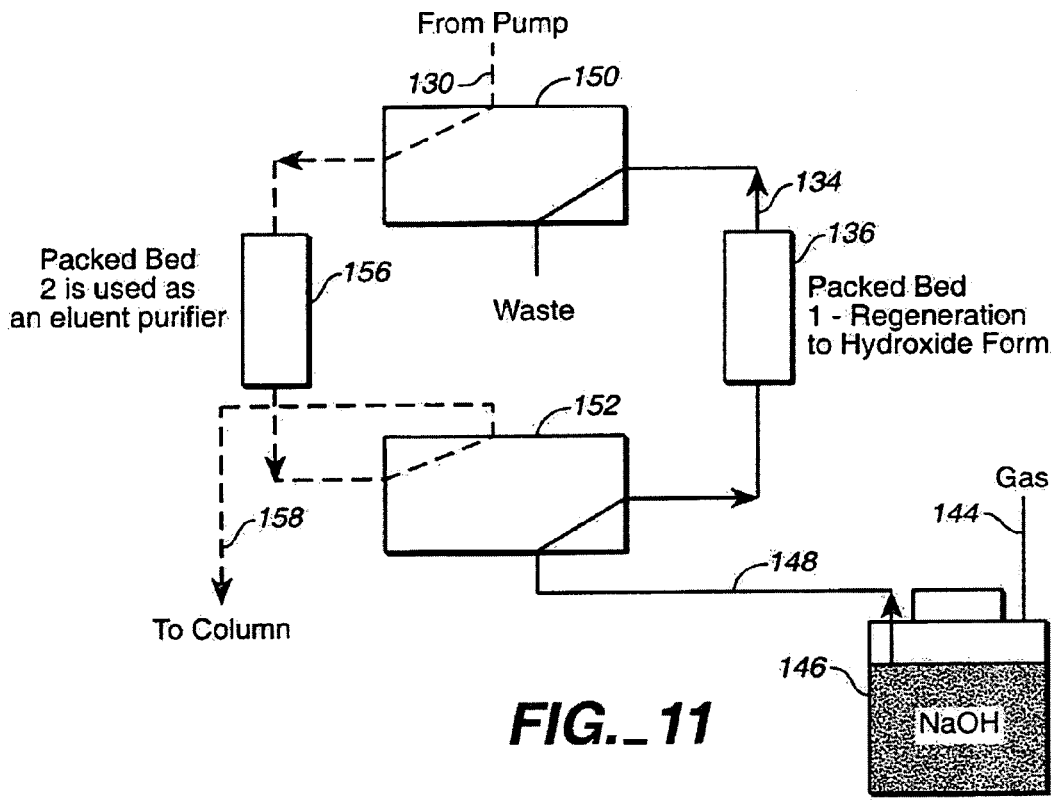
FIG._11
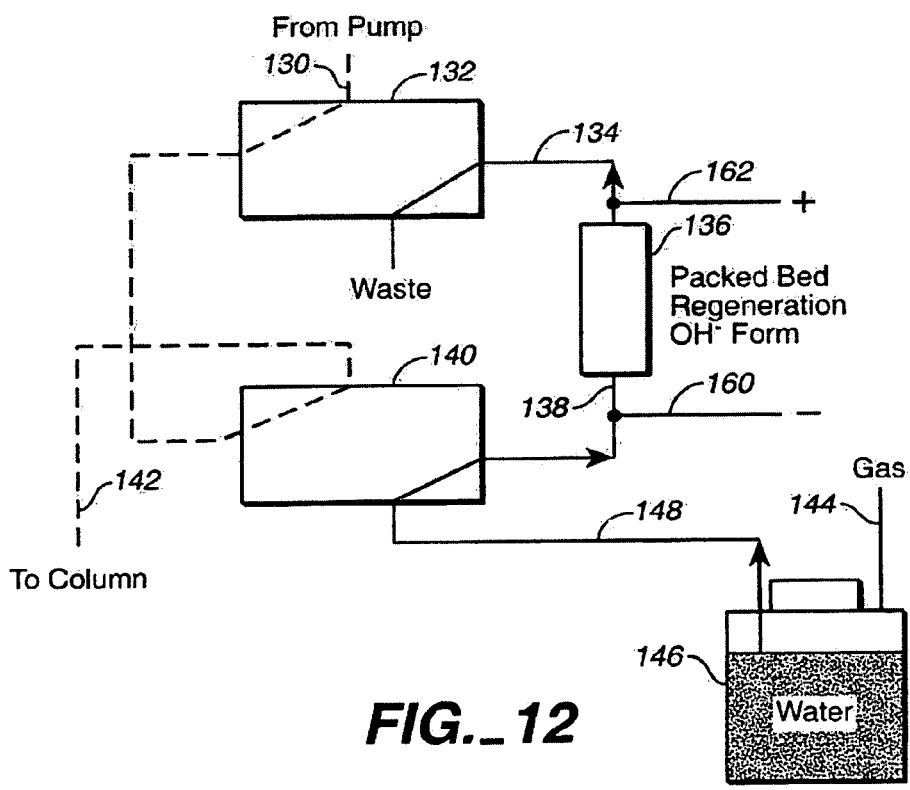
FIG._12

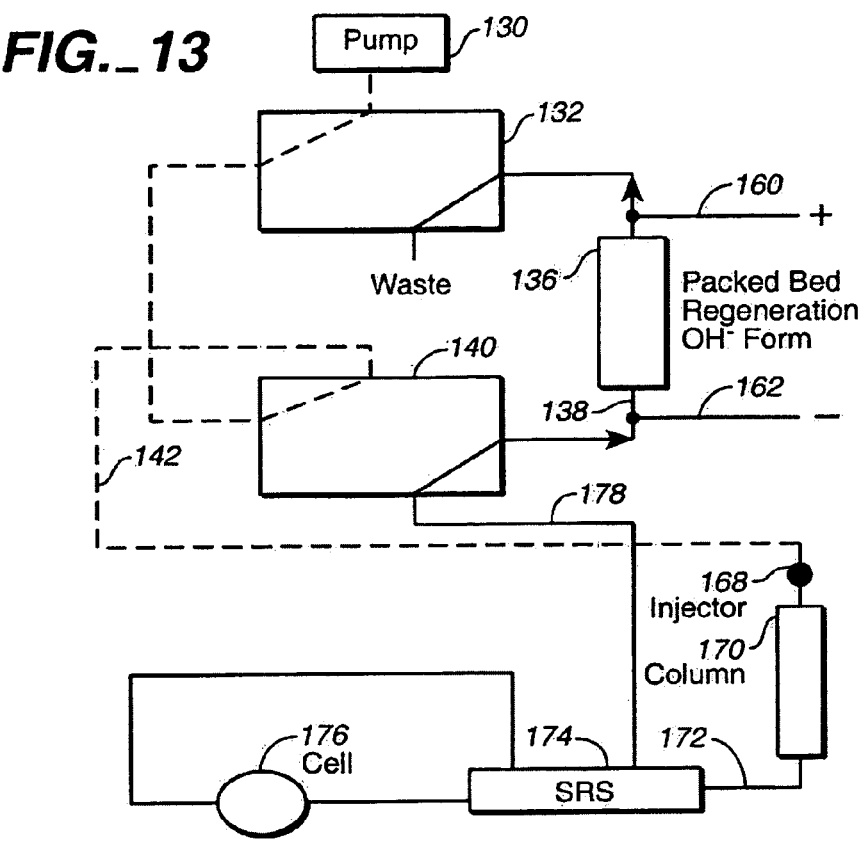
FIG._13
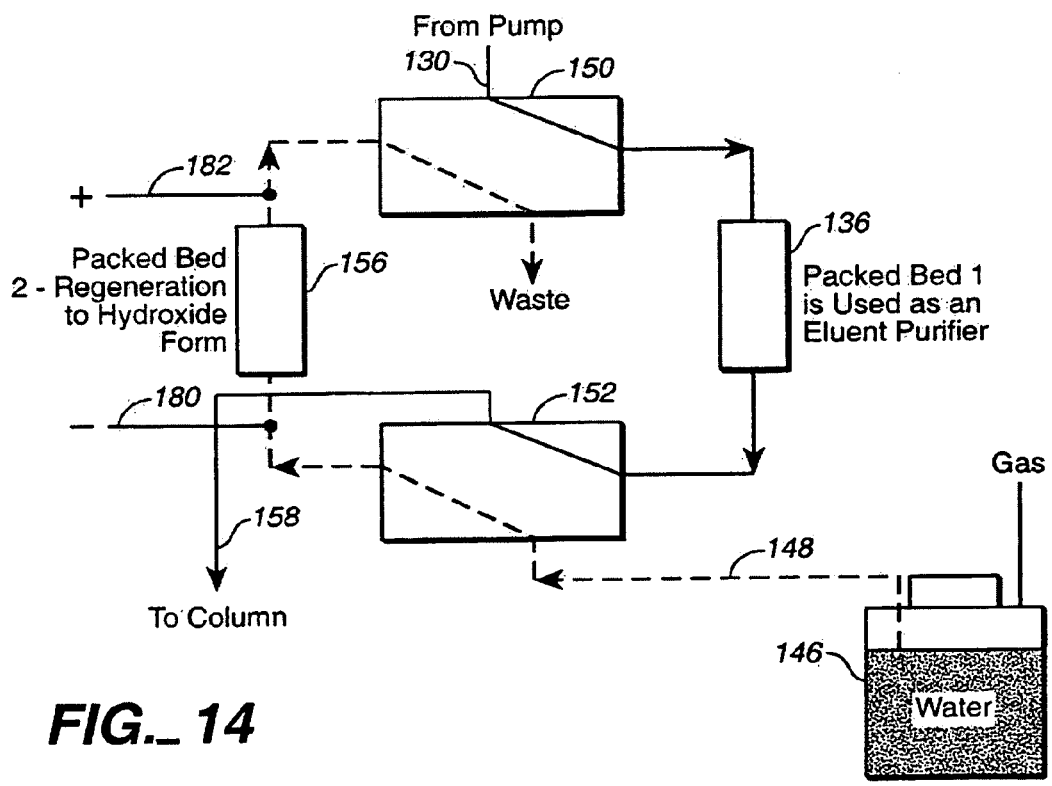
FIG._14

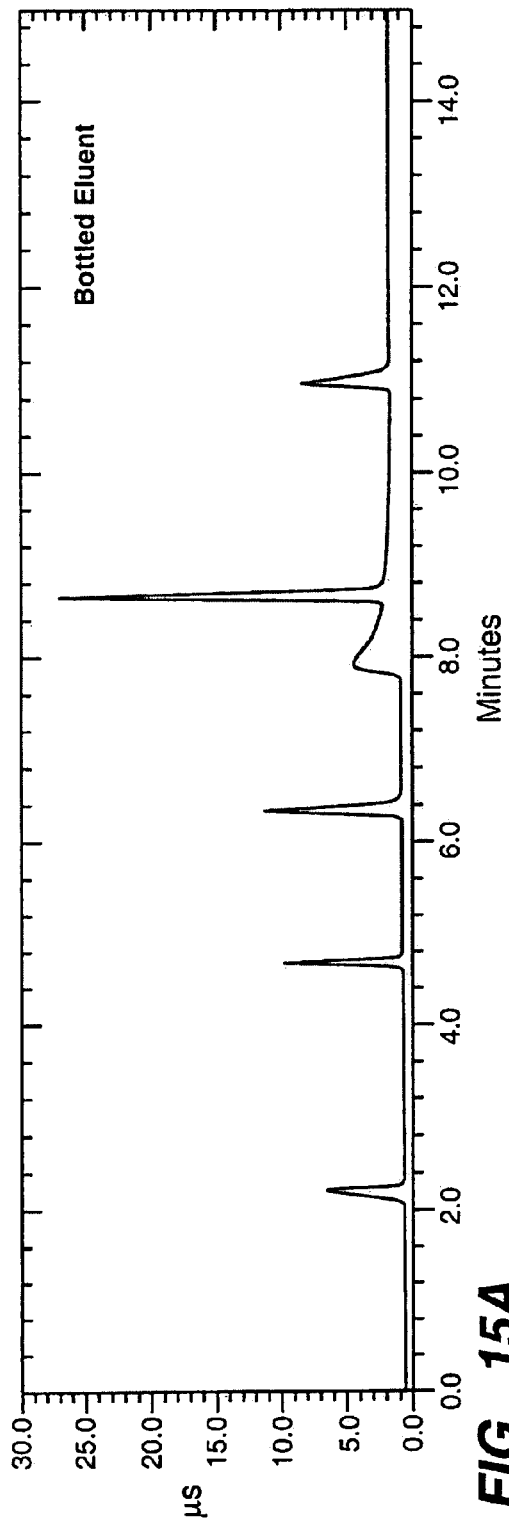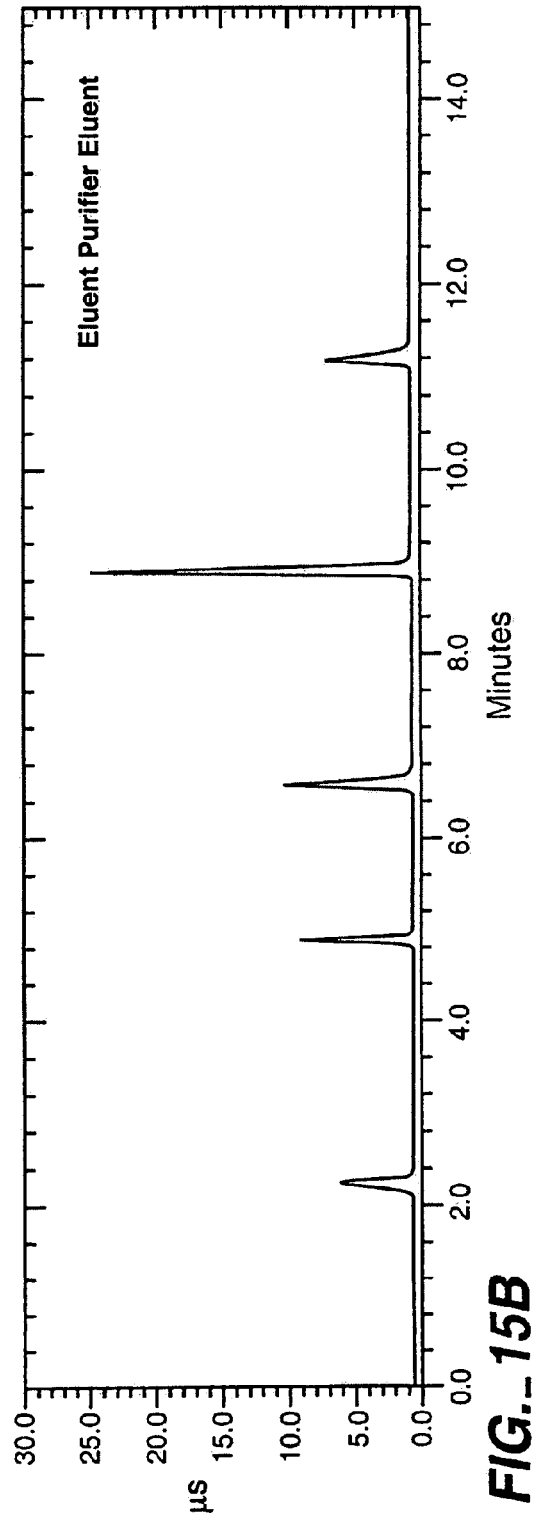

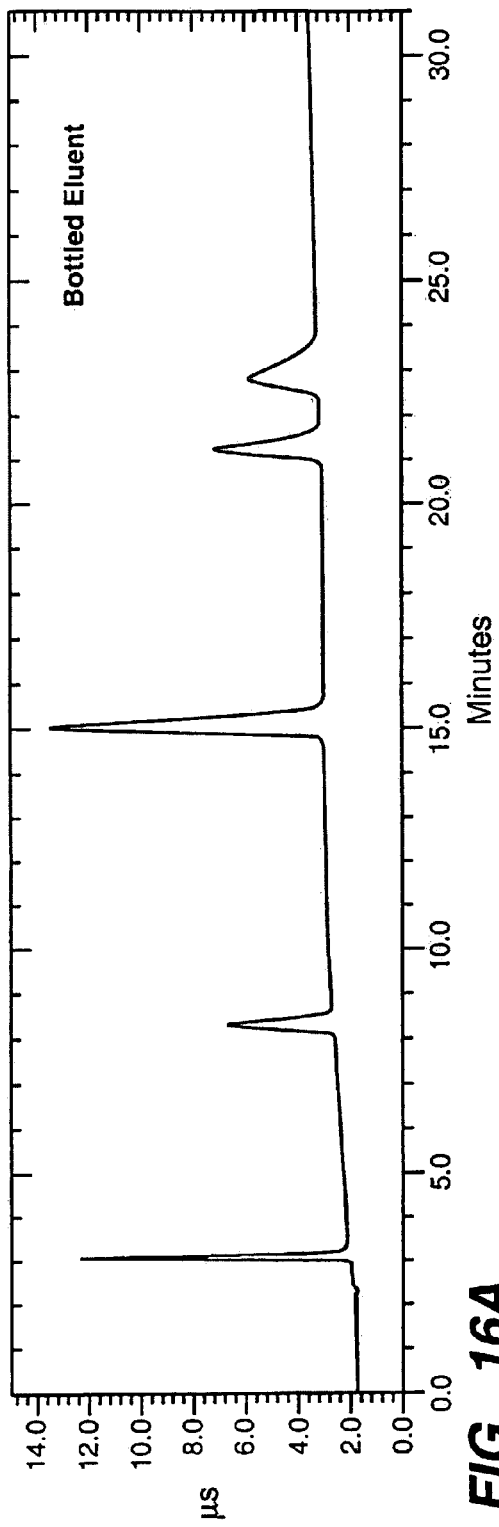
FIG._16A
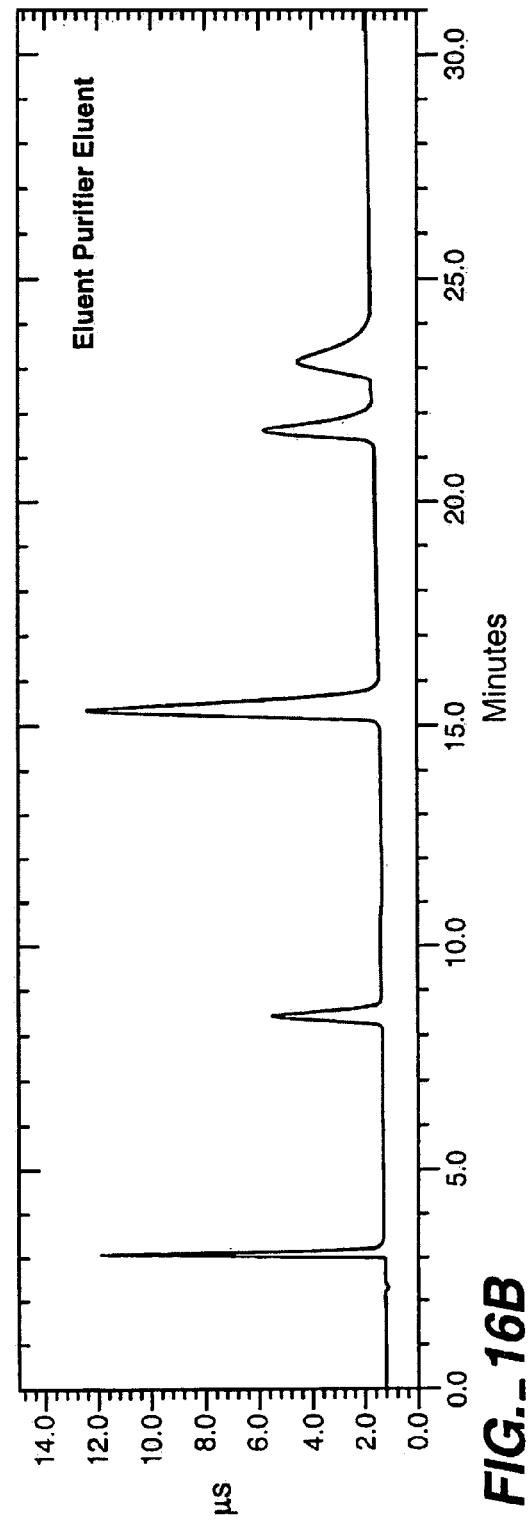
FIG._16B

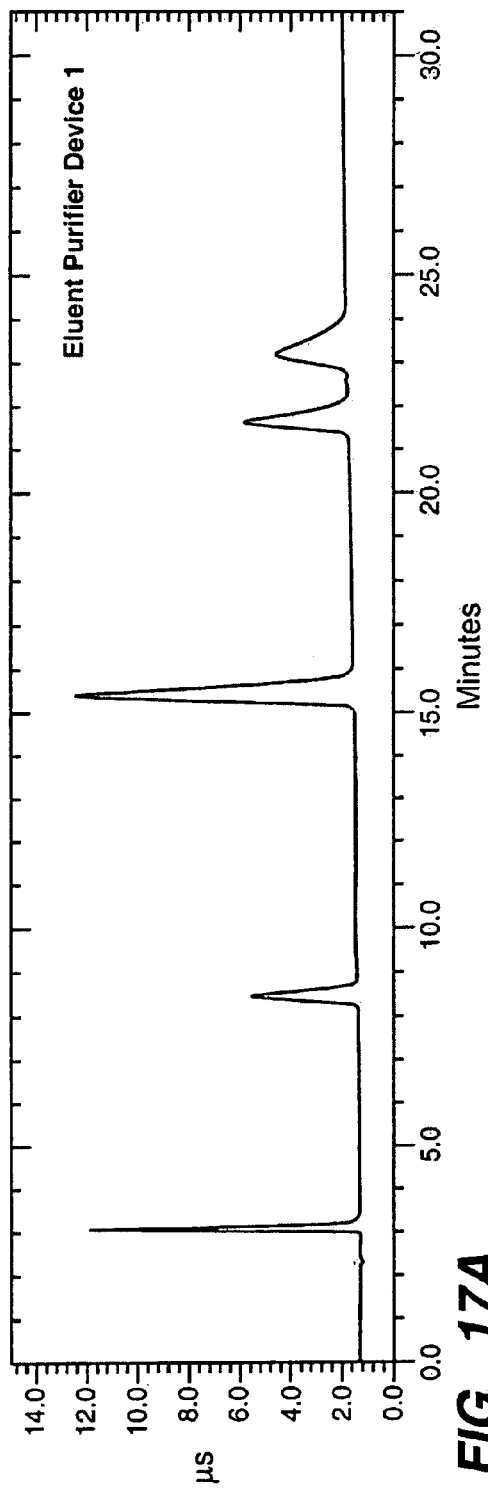
FIG._17A
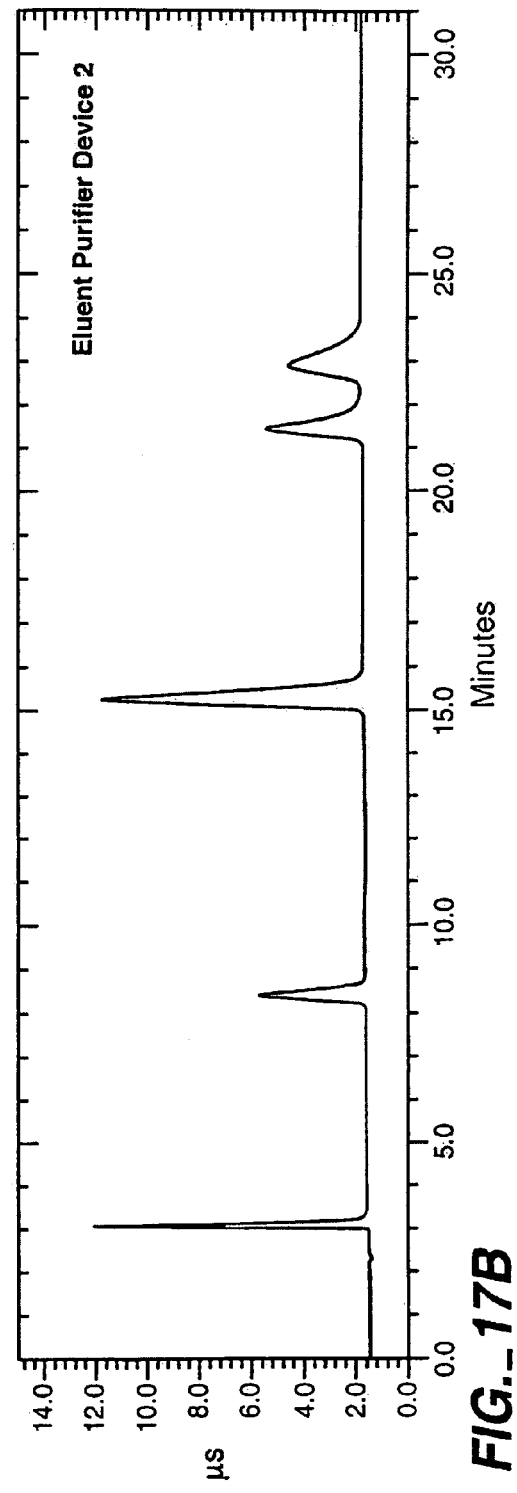
FIG._17B

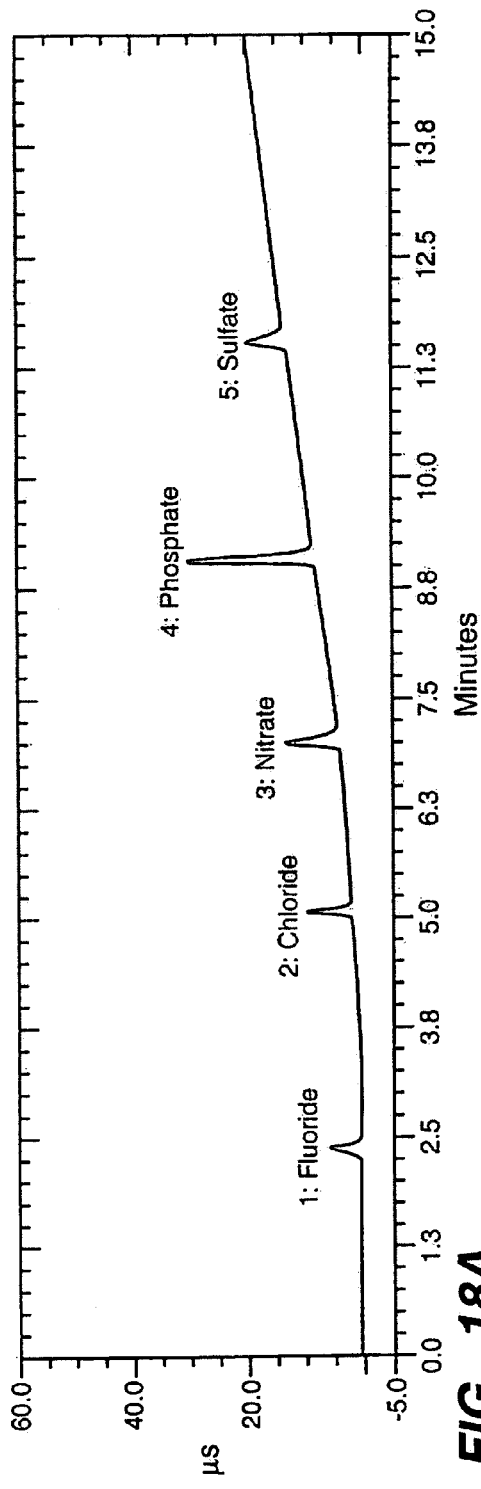
FIG._18A
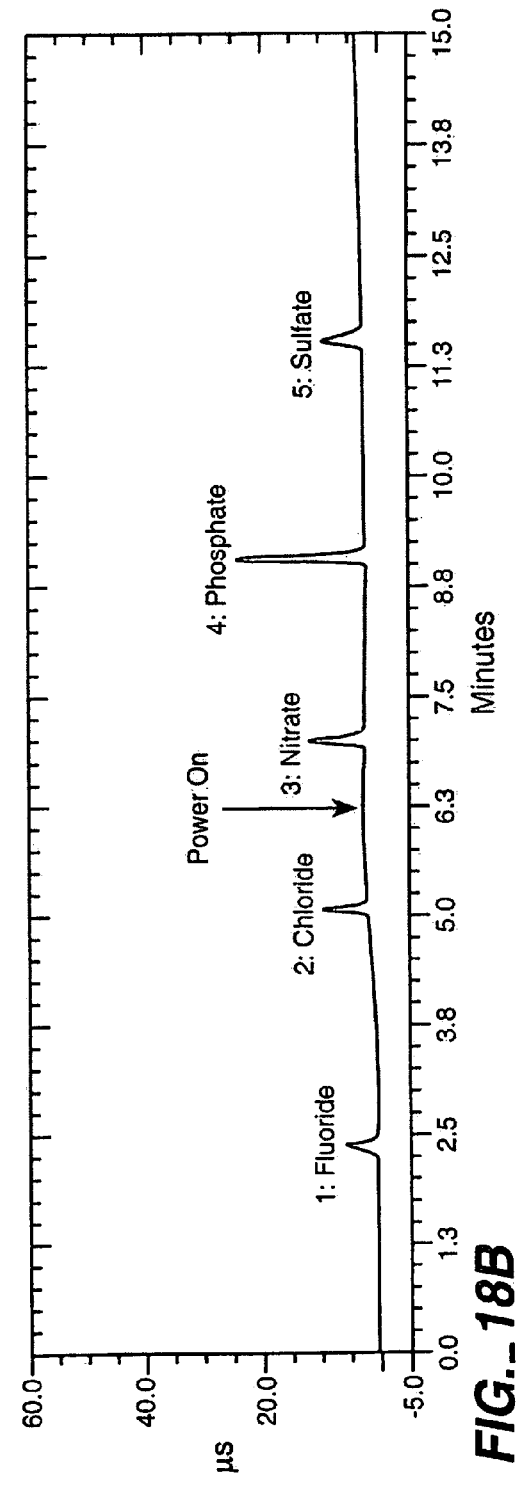
FIG._18B

AQUEOUS STREAM PURIFIER AND METHOD OF USE

CROSS-REFERENCE TO RELATED APPLICATION

This application is a continuation-in-part of pending U.S. application Ser. No. 10/043,645 filed Jan. 10, 2002.

BACKGROUND OF THE INVENTION

Concentrated acids or bases are commonly used as developing reagents in eluents for chromatographic separations. Ionic contaminants in the eluents can adversely affect chromatographic performance, particularly when performing ion chromatography analysis. For example, anionic contaminants such as carbonate ions from dissolved carbon dioxide gas on sodium hydroxide eluent used for anion analysis, can lead to high background noise. This problem can lead to baseline shifts during gradient analysis creating difficulties in integrating peaks leading to erroneous quantitation. One approach to addressing this problem is the use of the ION-PAC® anion trap column sold by Dionex Corporation disposed between the eluent pump and a sample injector. The column is filled with anion exchange resin material for the purpose of reducing contaminants such as carbonate ions by retention on the resin. However, such columns have limited capacity and do not operate continuously, thus requiring offline regeneration such as by flowing carbonate-free hydroxide through the resin for conversion to the hydroxide form. This approach can be costly and time consuming.

Other approaches to the generation of a high purity eluent use electrolytic conversion of a purified water stream. Such approaches are described in U.S. Pat. Nos. 5,045,204, 6,225,129 and 6,036,921. However, all of these approaches require a high purity water stream.

There is a need to provide an efficient method for purifying such eluents by contaminant removal.

SUMMARY OF THE INVENTION

In one embodiment, an electrolytic method is provided for purifying an aqueous stream, said aqueous stream including at least one contaminant ion, said method comprising (a) flowing said aqueous stream through a purifying flow channel having an inlet and an outlet, (b) applying an electric field through said flowing aqueous stream in said purifying flow channel between first and second spaced electrodes of opposite charge, said first electrode being of opposite charge to said contaminant ion, and (c) removing said contaminant ion from said aqueous stream in said purifying flow channel to produce a purified aqueous stream which flows out said flow channel outlet while drawing said contaminant ion toward said first electrode.

In another embodiment, the method comprises (a) flowing said aqueous stream through flow-through ion exchange medium having exchangeable ions of the same charge as said contaminant ion in a first purifying flow channel having an inlet and an outlet, (b) removing said contaminant ion from said aqueous stream in said flow channel to produce a purified aqueous stream which flows out said flow channel outlet, (c) discontinuing the flow of said aqueous stream through first purifying flow channel, (d) directing said aqueous stream through flow-through ion exchange medium having exchangeable ions of the same charge as said contaminant ion in a second purifying flow channel, and (e) regenerating the ion exchange medium in said first purifying flow channel by flowing an aqueous regenerant solution therethrough.

In a further embodiment, the method comprises (a) flowing said aqueous stream through flow-through first ion exchange medium having exchangeable ions of the same charge as said contaminant ion in a purifying flow channel having an inlet and an outlet, (b) removing said contaminant ion from said eluent stream in said purifying flow channel to produce a purified aqueous stream which flows out said purifying flow channel outlet, (c) flowing a first liquid sample stream analyte of the same charge as said contaminant ion and said purified aqueous stream from said purifying flow channel through chromatography separation medium having exchangeable ions of the same charge as said contaminant ion, and (d) after completion of step (c), and before flow of a second liquid sample stream through said chromatography separation medium, regenerating said ion exchange medium in said purifying flow channel by flowing an aqueous regenerant liquid stream through said purifying flow channel.

The invention also relates to chromatography apparatus for using devices for purifying according to such methods and comprising (a) at least one contaminant ion-purifying housing defining at least one purifying flow channel having an inlet an outlet, (b) a source of an aqueous liquid stream, including at least one contaminant ion in liquid communication with said purifying flow channel inlet, (c) spaced first and second electrodes of opposite charge disposed to apply an electric field through said one purifying flow channel, and (d) chromatographic separation medium having an inlet and an outlet, with exchangeable ions of the same charge as said contaminant ion, positive or negative, said separation medium inlet being in liquid communication with said one purifying flow channel outlet.

Another embodiment of chromatography apparatus according to the invention comprises (a) a source of aqueous liquid comprising at least one contaminant ion, (b) at least one contaminant ion-purifying housing defining at least one purifying flow channel, (c) first flow-through ion exchange medium, having exchangeable ions of one charge, positive or negative of the same charge as said contaminant ion, disposed in said one purifying flow channel, (d) chromatographic separation medium having an inlet and an outlet, with exchangeable ions of the same charge as first flow-through ion exchange medium, said separation medium inlet being in liquid communication with said one purifying flow channel, (e) a source of regenerant solution, and (f) valving including at least a first and second position, permitting, in said first position, flow from said one purifying flow channel to said chromatographic separation medium but blocking flow from said regenerant source to said one purifying flow channel and permitting, in said second position, flow from said regenerant solution source to said one purifying flow channel but blocking flow from said one purifying flow channel to said chromatographic separator.

BRIEF DESCRIPTION OF THE DRAWINGS

FIGS. 1-14 are schematic representations of apparatus according to the present invention.

FIGS. 15-18 are chromatograms illustrating the present invention.

DETAILED DESCRIPTION OF THE PREFERRED EMBODIMENTS

Figure 5:
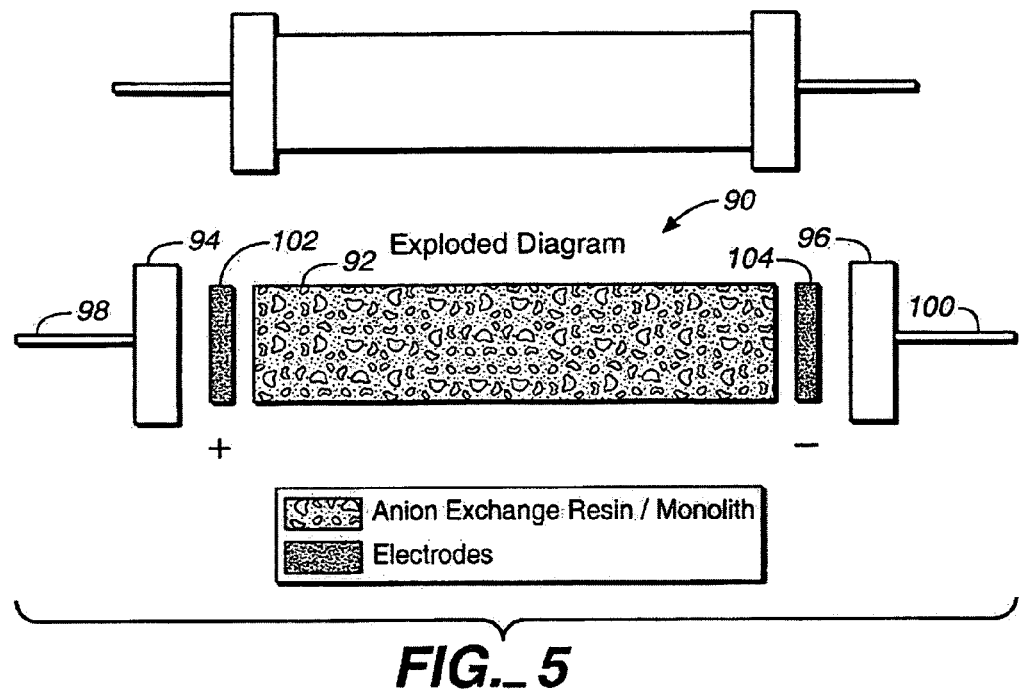

In accordance with a number of embodiments of the present invention, chromatographic suppressor devices and methods are adapted for eluent purification.

In one embodiment, an electrolytic method is provided for purifying an aqueous stream suitable for use as an eluent, e.g. suitable for use as a chromatography eluent or specifically, an ion chromatography eluent. In one embodiment, the electrolyte comprises selected ions of one charge, positive or negative, in the eluent stream and includes at least one contaminant ion of opposite charge to the electrolyte selected ions. Thus, for example, for anion analysis, an electrolyte comprises the cation of a base such as an alkali metal base (e.g., NaOH or KOH) and the contaminant ion of opposite charge to the electrolyte selected ions includes carbonate or bicarbonate ion. After removal of these contaminant ions, the eluent can be used in the foregoing types of chromatographic analysis systems. In another embodiment the eluent is an aqueous liquid stream which does not include an electrolyte but which can be used for electrochemical suppression. The invention is also applicable to the purification of an aqueous stream used for purposes other than chromatography. The terms "eluent" and "aqueous stream", used interchangeably, unless otherwise stated, refer to an aqueous stream which includes a contaminant ion of one charge, positive or negative, which is removed. For use as a chromatography eluent, the contaminant to be removed of the same charge as the analyte ions to be analyzed.

The invention first will be described with respect to an aqueous stream eluent containing an electrolyte.

In one embodiment, the contaminants are removed electrolytically. The eluent stream flows through a purifying flow channel of a contaminant ion-purifying housing. An electric field is applied through the flowing eluent stream in the flow channel between spaced electrodes of opposite charge. The contaminant ion is removed from the eluent stream to form a purified eluent which flows out the flow channel outlet while the contaminant ion is drawn toward the first electrode of opposite charge to the contaminant ion. This method will be referred to herein as the "electrolytic purifier."

Referring to FIG. 1, one form of the electrolytic purifier is schematically illustrated. Contaminant ion-purifying housing 10 defines a purifying flow channel 12, and includes an inlet 14 and an outlet 16. As illustrated, ion exchange resin 18, such as 8% cross linked Dowex resin, is disposed as a packed bed of resin particles in flow channel 12, typically in the form of a column such as an IONPAC® ion trapping column. Other flow-through ion exchange material can be used such as a liquid permeable monolith. Specifically, the monolithic may be of the type described in Example 7 of U.S. Pat. No. 6,027,643 or some other form in which liquid can flow through porous ion exchange material without excessive pressure drops. A significant difference from the ion trap column is the application of an electric field across the resin. Spaced electrodes of opposite charge are disposed to apply such field as across the resin bed 18 in flow channel 12. As illustrated, one electrode 20 is disposed at or near the exit from the flow channel while an electrode of opposite charge 22 is disposed in a position to apply an electric field across a portion of the resin bed. Electrode 22 is generally parallel to the flow of eluent through flow channel 12 and is disposed in an electrode chamber 26. Between electrode 22 and resin bed 18 is disposed a barrier 24 in the form of a charged perm selective membrane described below. Barrier 24 substantially prevents bulk liquid flow while providing an ion transport bridge for ions of the same charge as the contaminant ions. As illustrated, barrier 24 is transverse to flow across the flow channel 12. Electrode 22, barrier 24 and chamber 26 may be of the type described in FIG. 2 of U.S. Pat. No. 6,027,643. Electrodes 58 and 60 may be contained within different electrode chambers, not shown. Solution flowing through one of the chambers can be recycled to the other chamber to carry the electrolysis products to waste. A suitable DC power supply, not shown, connects the anode and cathode to provide a continuous electrical path between the anode and cathode through barrier 24 across the resin bed.

For simplicity of description, the invention will be described with respect to the purification of sodium hydroxide eluent by removal of carbonate ions. In this instance, the sodium hydroxide aqueous-eluent enters as a flowing stream through inlet 14. Resin bed 18 is an ion exchange medium in a packed bed or monolithic form including exchangeable anions, hydroxide or carbonate ion, of opposite charge to the electrolyte selected ion, sodium ion. In this instance, barrier 24 is an anionic exchange membrane with exchangeable ions of the same charge as the contaminant ions. The contaminant ions are drawn towards anode 22 disposed in electrode chamber 26. The electrolytic water splitting reaction occurs at the cathode to form hydroxide ions and hydrogen gas. An eluent purified of contaminant ion exits the flow channel. Anionic contaminants in the stream are trapped by ion exchange on the regenerated resin surface and are directed along with hydroxide ions towards the anode by the applied field and exit the device as an acid at the anode. The resin is simultaneously regenerated by the transport of hydroxide ions toward the anode.

In the illustrated embodiment, an aqueous solution either recycled from a downstream chromatography analysis system or from an independent source 28 flows into an inlet, not shown, of electrode chamber 26 and out an outlet 30. Water in electrode chamber 26 is electrolyzed to hydronium ions and oxygen and anionic contaminant ions, such as carbonate ions, are converted to carbonic acid or other acid for removal as a waste stream in outlet 30.

By increasing the current or potential applied to this device, transport of the contaminant ions are sped up thereby resulting in a reagent stream that is devoid of any anionic impurities. Since the eluent is diverted through the cathode formation of hydrogen gas occurs.

In one form of the invention, the purified eluent and the sample anions are directed to a conventional chromatography column for separation.

Referring to FIG. 2, the electrolytic purifier of FIG. 1 is used in an ion chromatography system wherein the suppressor is of the membrane type and the regenerant solution is used as a flowing stream for the electrode chamber of the electrolytic purifier to continuously remove the acid contaminant continuously. The eluent is pumped by pump 30 through an electrolytic purifier of the type illustrated in FIG. 1, including purifier housing 10 and electrode chamber 26. From there, the eluent can flow through a conventional degassing unit 32, e.g., of the type sold by Dionex Corporation, past a sample injector 34, into a chromatography column 36 and to a self-regenerating sandwich membrane suppressor 38 of the type described in U.S. Pat. No. 5,352,360 and of the type sold by Dionex Corporation under the SRS® name. The separated sample ions are detected, suitably by flowing through a conductivity cell 40 of a conductivity detector. Recycled aqueous liquid from the cell is utilized as the regenerant solution on the opposite side of the membrane as illustrated in the above patent. The regenerant solution from membrane suppressor 38 flows in line 42 through electrode chamber 26 and serves as the solution to carry away the acid and water formed in electrode chamber 26 so that the system can be operated continuously.

The effluent from chamber 26 flows in line 42 can be passed directly to waste or as illustrated in FIG. 2, can be used as the solution on the opposite side of a degassing membrane in a degassing apparatus, such as illustrated in U.S. Pat. No. 5,045,204, to carry the gas away from the purified effluent prior to passing to the chromatographic column 36.

As disclosed, the removal of the electrolytic gases from the purified eluent can be accomplished by methods disclosed in the prior art such as by flowing the purified eluent through gas permeable membrane tubings. An external sweep solution may be incorporated to aid removal of the permeated gas. It is also possible to apply vacuum on the outside of such gas permeable tubings. An alternate solution using the principles of Boyle's law is to compress the gas as disclosed in Small U.S. Pat. No. 6,316,270. This compression can be accomplished by increasing the chromatographic system backpressure by adding restriction tubing of small bore diameter such as 0.003" id PEEK tubings from Upchurch.

In another embodiment of the invention, the potential electrolysis gas problem is overcome by isolating the electrodes from the eluent pathway so that the gases are also isolated. This approach is illustrated schematically in FIG. 3. An eluent including sodium hydroxide and carbonate ion flows through purifier housing 50 containing an ion exchange medium in the form of a resin bed 52 through inlet 54. A barrier 56 formed of an ion exchange membrane, which may be of same type as membrane 24, is disposed adjacent anode 58 in an anode chamber, not shown. An aqueous stream flows through the cathode chamber. Carbonate and/or other anion contaminants are transported across barrier 56 into the anode chamber adjacent anode 58 so that carbonic acid is formed at anode 58. Electrolysis gas, oxygen, is formed at the anode isolated from the eluent flow. Eluent flowing into inlet 54 preferably is proximal to membrane 56 and flows into the inlet side of resin bed 52. On the opposite side of resin bed from membrane 58 is disposed anionic membrane 60 and cathode electrode 62 in a cathode chamber, not shown. The eluent solution flows from inlet 54 across resin bed 52 towards membrane 60 and out via outlet 64. Hydrogen gas generated electrolytically at the cathode is also isolated from the eluent stream. Thus, the purified eluent flowing out of outlet 64 does not have to be degasified because the electrolysis gases are isolated by the membrane.

Referring to FIG. 4, another form of the invention is schematically illustrated in which purification occurs in apparatus constructed like a commercially available SRS® sandwich membrane suppressor for cation applications sold by Dionex Corporation. Such an apparatus is illustrated in U.S. Pat. No. 5,352,360.

This system is illustrated using an eluent to be purified in the form of sodium hydroxide including carbonate contaminant flowing through the central flow channel 70 of membrane purifier 72. Channel 70 is defined by membranes 74 and 76 extending along the length of the flow path. As illustrated, the outside of the sandwich comprises solution flow channel 78 and 80. Cathode 82 and anode 84 are in electrical communication with flow channels 78 and 80. In the illustrated embodiment, membranes 74 and 76 are selectively permeable to anions but block cations and bulk liquid flow. The solutions in flow channels 78 and 80 can be water or other aqueous stream, which flows to waste.

The sodium ion in the eluent does not cross anion exchange membranes 74 and 76. In flow channel 78 adjacent cathode 82, water is electrolyzed to hydrogen gas (isolated from the eluent stream) and hydroxide. The hydroxide ions pass through membranes 76 into flow channel 70. The carbonate then flows across membrane 74 into flow channel 80 adjacent anode 84. There, water is hydrolyzed into hydronium ions and oxygen gas (isolated from the eluent stream). The hydronium ions and carbonate ions combine to form carbonic acid, which is carried out of the membrane suppressor in a waste stream.

Preferably, the flow in outboard channels 78 and 80 is countercurrent to the flow in eluent channel 70. The potential applied across electrodes 82 and 84 increases the kinetics of ion flow across the membranes to increase the efficiency of the transfer. The principles of operation of the membrane purifier are analogous to suppression as disclosed in U.S. Pat. No. 5,352,360 but for the purpose of purification. Suitably, a purifier of this type may be used on the low-pressure side of a pump.

Referring to FIG. 5, an electrolytic purifier is illustrated as similar to that of FIG. 3 but wherein the ion exchange bed is in direct contact with the electrodes in the flow pathway. Specifically, purifier 90 of this embodiment includes an ion exchange resin bed 92 held together by column end fittings 94 and 96 through which an inlet and outlet tubing 98 and 100, respectively, project. The ion exchange resin can be of the same type as discussed in FIG. 3. Flow-through anode 102 and cathode 104 are disposed at the inlet and outlet ends, respectively, of resin bed 92. The ion exchange bed 92 is in direct contact with the electrodes. The eluent is exposed to electrolytic gases, and so a degassing unit is preferably used in this embodiment. In this system, the carbonate ions are drawn to anode 102 away from the outlet while much of the bed is in the hydroxide form. Eventually, the bed becomes exhausted. Then, the polarity can be reversed and a liquid can flow through the system to regenerate the anion exchange resin. In one form of this system, the system can be combined with suitable valving with another ion exchange resin bed device of the same type so that one bed is being used while the other one is regenerated followed by switching. Switching can occur before or after each run or after five or more runs. This type of valving is illustrated hereinafter.

Figure 6:
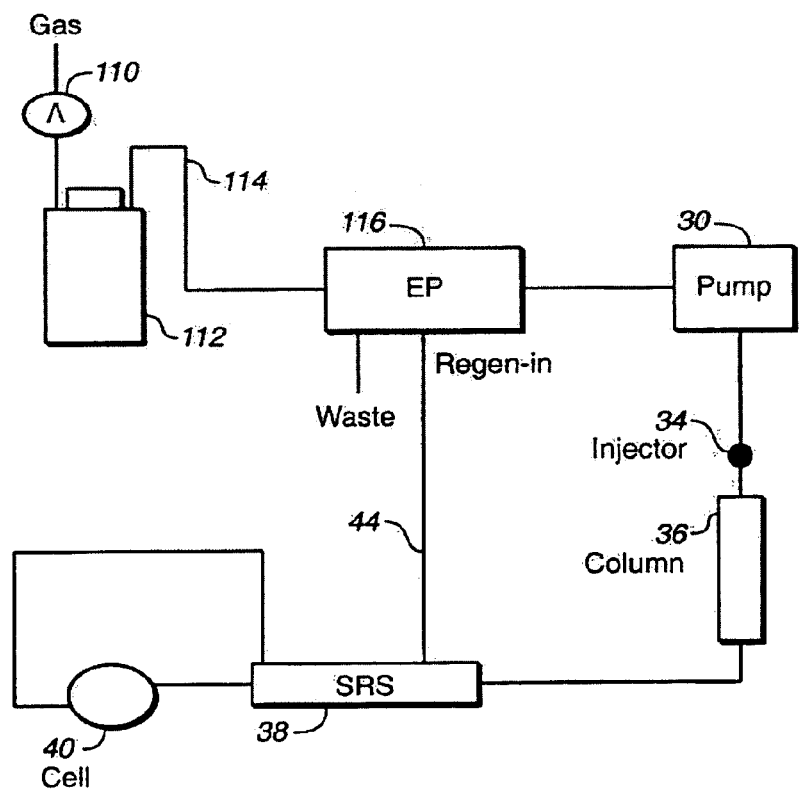

Referring to FIG. 6, an embodiment of the invention similar to that of FIG. 2 is illustrated in which an electrolytic purifier of the type illustrated in FIG. 4 is disposed on the low pressure side of the eluent pump. Like parts between FIGS. 2 and 6 will be designated with like numbers. Gas from source 110 forces the eluent solution in container 112 through line 114 into eluent purifier 116. Since the eluent is isolated from the purifier illustrated in chambers 78 and 80 illustrated in FIG. 4, there is no gas in the purified eluent and thus no need to use a degas assembly.

Referring to FIG. 7, another embodiment of the invention is illustrated in which the electrolytic purifier of FIG. 5 is used in combination with a degas assembly. Eluent from pump 120 flows through electrolytic purifier 90, flanked by electrodes, not shown, to a degas assembly 122 and from there through sample injector 34, through column 36, to a self-regenerating membrane suppressor of the type described above. Solution from the regenerant chamber of suppressor 38 flows through line 124 to the degas assembly and serves as the solution to carry the gas to waste. As discussed above in a typical degas assembly, e.g. as described with respect to FIG. 7 of U.S. Pat. No. 5,045,204, the eluent solution flows through a porous tubing and the gas permeates through the outer diameter of the porous the tubing into the solution outside the tubing to flow to waste in line 126.

All systems are illustrated for the purification of NaOH by eliminating anions such as carbonate. However, it is also applicable to other eluents such as KOH or other bases. Moreover, by reversal of polarity of the electrodes, and by the use of cationic membranes and ion exchange resin, cationic contaminants may be removed from acidic eluents used for cation analysis.

In all of the foregoing devices, electrolysis is employed to assist in the removal of the impurities from the eluent. A second aspect of the invention includes appropriate valving and one or more packed beds, which can be regenerated chemically or electrolytically. One difference of these embodiments from the prior art traps is that the system can operate continuously while alternate regeneration of one or more packed beds occur after one or more runs.

Referring to FIGS. 8 and 9, another embodiment of the invention is illustrated using a single packed bed and with valving to switch a purifier between online and regeneration modes, respectively. Referring first to FIG. 8, an eluent such as a NaOH is supplied at tubing 130 to valve 132, line 134 to a purifier 136 in the form of a packed bed of anion exchange resin initially in hydroxide form. Eluent from bed 136 flows through line 138 to valve 140 and from there in line 142 to a chromatography column, not shown, with an analyte for separation and detection as in a conventional chromatography or ion chromatography system. The system also illustrates a source of pressurized gas 144 to pressurize regenerant solution in reservoir 146, filled with NaOH or other hydroxide. The liquid in reservoir 146 is connected by tubing 148 to valve 140 and to valve 132 by tubing 150. In the valve position illustrated in FIG. 8, there is no flow from reservoir 146 to the purifier 136. In this valve position the flow of regenerant out of the reservoir 146 may be switched off by using a gas-switching valve (not shown) installed in line 144.

Referring to FIG. 9, the system of FIG. 8 is illustrated with the valving switched to a second position for regeneration of purifier 136. In this instance, there is no flow from pump 130 to the purifier 136. Here, the regenerant solution, NaOH, flows from valve 140 through line 138, purifier 136 and through valve 132 to waste. The valving can be selected to regenerate the packed bed after each chromatographic run or multiple runs if desired. If done after each run, regeneration can occur frequently without the need for a second column. This has the advantage of not permitting the bed of resin in purifier 136 to become so depleted of hydroxide ion that eluent contamination could interfere with chromatographic analysis. In this instance, purifier 136 is shown on the high pressure side of the pump. It may also be used on the low pressure side of the pump.

Referring to FIG. 10, another embodiment of the invention is illustrated using chemical regeneration and two packed bed purifiers with valving to alternate flow between online use and regeneration. Detail of suitable valving used for suppression is illustrated in U.S. Pat. No. 5,597,734. Like parts in the system with respect to FIGS. 8 and 9 will be designated with like numbers for the system of FIG. 10. In this instance, valves of similar type to FIGS. 8 and 9 with connecting elements will be designated 150 and 152. Here, valve 152 is connected by line 154 to a second packed bed purifier 156 and to line 158 back to valve 150.

As illustrated in FIG. 10, flow from a pump, not shown, in line 130 flows through valve 150, line 134, through online purifier 136, valve 152 and line 158 to a chromatography column. Simultaneously, regenerant solution from reservoir 146 flows through line 148 to a second packed bed purifier 156 to regenerate the same. The effluent from purifier 156 flows in line 158 through valve 150 and to waste.

At the desired interval, the positions of valve 150 and 152 are reversed for regeneration. Regenerant solution from reservoir 146 flows through line 148, valve 152 to purifier 136 for regeneration and through line 134, and valve 150 to waste. Simultaneously, eluent solution from a pump flows through line 130, valve 150 through purifier 156, valve 152, line 158 and to a chromatography column. As set forth above, the systems can be regenerated after each chromatography run or several or more runs by switching the valve settings at appropriate intervals.

In another embodiment of the invention, illustrated in FIG. 12, a device with valving of the type illustrated in FIG. 8 is employed with the exception that regeneration is performed electrolytically and the solution in reservoir 146 can be water rather than NaOH. Like parts will be designated with like numbers between FIG. 8 and FIG. 12. Cathode 160 disposed at the inlet of the packed bed in purifier 136 and anode 162 is disposed at the outlet end of purifier 136 suitably is in the form illustrated in FIG. 5 but is illustrated in FIG. 12 in the regeneration mode. Regeneration can occur with any desired frequency such as after each run by electrolytic operation using water from supply 146 or some other supply. The device is electrically polarized during regeneration and the electrolytically formed ions regenerate the packed bed.

In another embodiment of the device illustrated in FIG. 13, the aqueous liquid used to regenerate the packed bed eluent purifier is supplied from a self-regenerating sandwich membrane suppressor as illustrated in U.S. Pat. No. 5,352,360. Like parts between FIGS. 12 and 13 will be designated with like numbers. With purifier 136 online, eluent in line 142 flows past injector 168 through column 170 to separate analytes and then through line 172 to suppressor 174 through detector 176. For regeneration, the valving is reversed and the aqueous solution in the regenerant flow channel on the other side of the membrane from the sample flow channel in suppressor 174 flows through line 178 through valve 140 and line 138 to purifier 136. The electrodes are activated and the packed bed is electrolytically regenerated as set forth above. Thus, the detector cell effluent is used for electrolytic regeneration and then sent to waste. In an alternative embodiment, not shown, the liquid stream from cell 176 can be diverted to line 178 to regenerate packed bed 136, with the aqueous waste fluid diverted to suppressor 174 in the recycle mode, as illustrated in U.S. Pat. No. 5,352,360.

Another embodiment illustrated in FIG. 14 is similar to that of FIG. 11 in that one purifier is online while the other one is regenerated. The difference is that regeneration is performed electrolytically and so water can be used in the reservoir as the solution for regeneration. Like parts will be designated with like numbers. In the illustrated valve position, water from reservoir 146 flows through line 148 to valve 152 into packed bed purifier 156 and valve 150 to waste. Cathode 180 is disposed on the inlet side of purifier 156 and 182 on the outlet side to permit electrical regeneration of the packed bed in purifier 156. Simultaneously, other purifier 136 is online as illustrated. Electrodes, not shown, of the type illustrated for purifier 156 are used with purifier 136 but inactive in this valve setting. At a selected interval such as after-each run, the valving is switched. The lines can be switched from one to the other by including appropriate mode of electrolytic regeneration to both purifiers but the voltage is only applied to the purifier being regenerated.

The valving of the present invention is described with respect to the selective flow of a regenerant solution through the purifier (water for an electrolytic system and acid or base for a chemical system). However, appropriate valving, not shown, could be used to selectively flow an aqueous rinse solution through the purifier, e.g., after regeneration with acid or base in accordance with the present invention.

In another embodiment of the invention; the electrolytic suppressor disclosed in EP 1,074,837 can be adapted for continuous purification and regeneration by flowing the eluent solution through the disclosed suppressor. In this embodiment, a barrier to bulk liquid flow is not required between the electrodes and the ion exchange resin bed.

In another embodiment, the foregoing method and apparatus can be used for removing anions and/or cations from an aqueous stream that does not include a developing electrolyte but which includes contaminant ions of the same charge as the analyte ions, positive or negative. The removed anions are replaced with electrolytically generated hydroxide ions and the removed cations are replaced with electrolytically generated hydronium ions. Such a purified water stream is suitable for ion chromatography analysis as a water stream for eluent generation or eluent dilution or as a sample diluent.

In ion chromatography with an eluent generator module, a water stream is pumped into the eluent generator module to generate online eluents electrolytically. Such approaches are described in U.S. Pat. Nos. 5,045,204, 6,225,129 and 6,036,921. The water stream that is diverted into the eluent generator module could be purified of contaminating cations or anions using the devices of the present invention. For anion analysis, the contaminating anions in the water stream such as carbonate and chloride will be removed by the eluent purifier modules of the present invention. In suppressed ion chromatography, the remaining cations in the water stream will be suppressed by the suppressor hence low background is achievable with the present invention.

The water stream in a laboratory or process environment could be contaminated due to a variety of reasons. The water stream during collection from a water purifier is exposed to atmospheric air and this result in dissolution of air borne contaminants such as carbon dioxide gas. The use of a carbon dioxide contaminated water stream for eluent generation would impact performance during ion chromatography analysis. Similarly depending on the extent of purification, the water stream will have residual ions that would increase the conductivity background and impact performance and response during ion chromatography analysis. The variations in water quality from laboratory to laboratory and from day to day can be minimized by using the method and apparatus of the present invention.

In sample preparation applications there is a need for contaminant free water for the purpose of diluting the samples and for calibration purposes. This type of dilutions can be done online using automated auto samplers or offline. The devices of the present invention could be used for this sample preparation purpose. When an anion purifier of the present invention is coupled to a cation purifier of the present invention water free from standard ionic contaminants can be achieved.

Various types of water can be further purified by the devices of the present invention such as laboratory deionized water, reverse osmosis water, municipal tap water and the like.

All patents and other publications referred to herein are incorporated by reference.

In order to illustrate the present invention, the following examples are provided.

EXAMPLES

Example 1

A DX500 Ion chromatography system was used for anion analysis. The analytical column was an AS11 column 4×250 mm, which was operated with the following gradient (0.5-38.25 mM).

| E1 | DI water | Flow = 2 ml/min | |
|---|---|---|---|
| E2 | 5.0 mM NaOH | | |
| E3 | 100 mM NaOH | | |

| Time | E1 | E2 | E3 |
|---|---|---|---|
| 0 min | 90 | 10 | 0 |
| 2 min | 90 | 10 | 0 |
| 5 min | 0 | 100 | 0 |
| 15 min | 0 | 65 | 35 |

The suppressor was a Dionex ASRS Ultra™ suppressor that was operated at an applied current of 100 mA in the normal recycle mode. In this example, the comparison of prior art approach to the present invention is shown.

The eluent purifier design was similar to FIG. 1 and the plumbing schematic was similar to FIG. 2. The eluent purifier was packed with 20 μ fully aminated vinylbenzylchloride-8% divinylbenzene resin in the hydroxide form. The ion exchange membrane in this example was an anion exchange membrane AMI-7001 from Membrane International, N.J. When the bottled eluent was used without the eluent purifier, a commercially available trap column from Dionex Corporation was used in place of the eluent purifier. The applied current to the eluent purifier was 40 mA and the voltage was roughly 35V.

A mixture comprising 5 anions was injected and analyzed. FIG. 15 compares the results obtained from this study. A peak corresponding to carbonate was detected prominently when the eluent purifier was not used. The presence of this peak also impacted integration of sulfate, which eluted in close proximity to carbonate. The eluent purifier on the other hand did not have this issue. Sulfate was integrated better on the eluent purifier run as there was not shift in the baseline from carbonate contamination.

The bottled eluent showed excessive shifts in the background. The drift observed for 15 minutes was roughly 1.05 uS/cm for the bottled eluent. The eluent purifier on the other hand showed no major shifts in the baseline. The typical drift observed for a 15 minute period was roughly 0.165 uS/cm. Thus, the eluent purifier showed superior performance when compared to a bottled eluent with a conventional trap column.

Example 2

The experimental setup was similar to Example 1 with the eluent purifier online. In this example, the chromatographic performance reproducibility was studied. The reproducibility of the separation parameters from this testing (n=34 runs) could be inferred from the following: % RSD peak retention time=0.18%; % RSD peak ht=0.57%; % RSD peak area=0.43%. The above results demonstrate excellent reproducibility of the eluent purifier.

Example 3

The experimental setup was similar to Example 1 with the eluent purifier online. The analytical column was an AS10 4×250 mm column, which was operated with the following:

| | | |
|---|---|---|
| E1 | 50 mM NaOH | |
| E2 | 200 mM NaOH | |
| Time | E1 | E2 |
| 0 min | 100 | 0 |
| 31 min | 38 | 62 | gradient (50 mM - 153 mM NaOH).

The suppressor was an ASRS Ultra suppressor that was operated at an applied current of 300 mA in the normal recycle mode. In this example, the comparison of prior art approach to the present invention is shown.

The eluent purifier design was similar to FIG. 1 and the plumbing schematic was similar to FIG. 2. When the bottled eluent was used without the eluent purifier, a commercially available trap column from Dionex Corporation was used in place of the eluent purifier. The applied current to the eluent purifier was 100 mA and the voltage was roughly 35V.

A mixture comprising 5 anions were injected and analyzed. The bottled eluent showed excessive shifts in the background as shown in FIG. 16. The drift observed for 31 minutes was roughly 1.75 μS/cm for the bottled eluent. The eluent purifier on the other hand showed a drift for a 31 minute period of roughly 0.670 μS/cm. Clearly, the eluent purifier showed superior performance when compared to a bottled eluent with a conventional trap column for this high concentration gradient. Note that the bottled eluent runs progressively became worse since the device capacity was exceeded due to the high ionic strength making it not very suitable for this application.

Example 4

The experimental setup was similar to Example 3 with an eluent purifier online. Here, performance of two different eluent purifiers was compared using the same gradient shown in Example 3. The results indicate excellent device-to-device reproducibility of this approach as shown in FIG. 17.

Example 5

In this example, the device of FIG. 3 was used as the eluent purifier. All other conditions were similar to Example 1 except there was no need to use the degas module. The electrodes were swept sequentially from the cathode followed by the anode by the SRS waste.

The line from the anode was diverted to waste. The results from these runs were similar to the eluent purifier run from FIG. 1 and low drift was observed during the gradient run.

Example 6

In this example, the device of FIG. 4 was used. The anion exchange membranes and screens were radiation grafted TEFLON® and polyethylene materials, respectively. The gaskets for the screens in this device were made from parafilm. This device was plumbed in the low pressure side of the pump as shown in FIG. 6. Since the eluent was isolated from the regenerant chamber, there was no gas in the purified eluent, hence there was no need to use a degas assembly. This device reduced the background similar to the other devices of the present invention suggesting excellent removal of anionic contaminants from the eluent stream.

Example 7

In this example, a device of FIG. 1 was used except the anion exchange resin and membrane were replaced with a cation exchange resin (20μ sulfonated polystyrene/8% divinylbenzene in the H+ form) and membrane (AMI-7000 a cation exchange membrane from Membrane International, N.J.). The electrode on top of the membrane was designated the cathode in this example. The outlet electrode was designated the anode. This device was now suited for removing cationic impurities from the eluent, preferably acidic eluents.

Example 8

This example shows anion analysis with a device of the present invention. A packed bed device with is a 4×35 mm column is fitted with flow through electrodes, and is packed with 20μ fully aminated vinylbenzylchloride-8% divinylbenzene resin in the hydroxide form (as shown in FIG. 5). The device was connected to a degas assembly and then connected to the rest of the system as shown in FIG. 7. The device was first tested without polarization and showed excessive shifts similar to prior art trap column devices as shown in FIG. 18A. When the device was powered, the device started purifying the eluent as soon as the power was applied as shown in FIG. 18B. The net result of applying the power according to the present invention improved the device capacity and its ability to remove ionic contaminants. The useful life of the packed bed device is extended.

Example 9

This example shows anion analysis with a device of the present invention. In FIG. 8, a packed bed device, which is a 4×35 mm column, is packed with 20μ fully aminated vinylbenzylchloride-8% divinylbenzene resin in the hydroxide form, is used for removing anionic contaminants from the eluent. The device may be regenerated chemically by rinsing with sodium hydroxide after each run or may be regenerated after several runs as shown in FIG. 9, thus allowing continuous operation. In this figure, the device is shown on the high pressure side of the pump. It is also possible to implement the above design on the low pressure side of the pump. In this example, the packed bed device is regenerated chemically. The above device is suited for removing anionic impurities from a reagent stream.

Example 10

This example shows anion analysis with a device of the present invention. The packed bed is similar to the one shown in Example 9, except in this case two packed bed devices are used for purifying the eluent. One packed bed is being regenerated as shown in FIG. 10, while the other packed bed is used for the purification process. Again, after several runs or after each run, the packed beds reverse their roles and this is shown in FIG. 11 where packed bed 2 now becomes the purifier while packed bed 1 is being regenerated. Thus, switching between the two packed bed devices enables continuous uninterrupted operation.

Example 11

This example shows anion analysis with another device of the present invention. In this case, a packed bed with electrodes as shown in FIG. 5 is used. The device is packed with 20μ fully aminated vinylbenzylchloride-8% divinylbenzene resin in the hydroxide form. The device can be used as shown in FIGS. 10 and 11, with the exception that sodium hydroxide reagent is replaced with water. The device may be regenerated after each run or may be regenerated after several runs by electrically polarizing the packed bed. By regenerating this device offline, there is no need to deal with electrolytically generated gases, thus allowing continuous operation. The regeneration of this device is shown in FIG. 12. Also note that in this figure the device is shown on the high pressure side of the pump. It is also possible to implement the above design on the low pressure side of the pump. In this example, the packed bed device is regenerated electrolytically and requires a power supply to polarize the electrodes. The water required for the electrolytic process can be derived by pumping in the SRS wastes, thus eliminating the need for maintaining an external source of water as shown in FIG. 13. One could also divert the cell effluent first into this device for electrolytic regeneration following which it is diverted back to the SRS regen-in port and then diverted to waste.

Example 12

This example shows anion analysis with another device of the present invention. In this case, a packed bed with electrodes as shown in FIG. 5 is used. The device is packed with 20μ fully aminated vinylbenzylchloride-8% divinylbenzene resin in the hydroxide form. The device can be used as shown in FIGS. 10 and 11 in a switching mode with water instead of sodium hydroxide as the regenerant. The device is electrically polarized during regeneration step where the electrolytically formed ions regenerate the packed bed as shown in FIG. 14. Again, regeneration could be done after every run or after several runs, thus enabling continuous operation. The water required for the electrolytic process can be derived by pumping in the SRS wastes, thus eliminating the need for maintaining an external source of water. One could also divert the cell effluent first into this device for electrolytic regeneration following which it is diverted back to the SRS regen ports and then to waste.

Example 13

Using the apparatus of FIG. 1 an aqueous stream without a developing electrolyte flows into inlet 14. The anionic contaminants are removed and replaced with hydroxide. Such a water stream is used to generate base using an eluent generator module. DI water is pumped into the purifier device and the purified water is diverted into a commercially available EG40 module from Dionex Corporation, and located fluidically between the purifier device 10 and the degas module 32. A Dionex eluent generator EG40 module generates base required for anion analysis. The purifier module purifies the DI water from anionic contaminants. The cationic contaminants are all suppressed in a suppressor and the conductivity cell detects a lower background due to the removed contaminants.

Example 14

A DI water sample stream spiked with anionic contaminants ranging from 20 to 150 ppb of various anions is pumped into a purifier device of the type illustrated in FIG. 1 and the purified stream was diverted into a TACLP1 concentrator column from Dionex. 30 ml of the purified stream was concentrated on the concentrator column and then analyzed using a DX500 system and AS15 chemistry with 38 -mM NaOH eluent at 1.2 ml/min flow rate. An ASRS Ultra suppressor was used at 125 mA for this application. The purifying device removed trace anionic impurities from water. The removal efficiency was >99.9% for all seven anions.

Example 15

A DX500 system was used for the cation analysis of house RO water. The water container was exposed to ambient laboratory conditions for several hours before analyzing the contents of the container. Cation analysis was done pursuing standard CS12A chemistry using 20 mM MSA eluent at 1 ml/min flow rate. The cation suppressor was a Dionex CSRS Ultra and was run at 100 mA for this application. A cation purifier device, which is designed to remove cations, was used for this work. The same water when purified using the cation purifier device shows excellent removal efficiency for all ions. Several unknown contaminant peaks were removed by the purifier device illustrating the utility of the device of the present invention for water purifying applications.

Example 16

The purifier devices of example 14 and example 15 are combined together in this example. The water stream is pumped into these modules and the resulting purified water is collected for use with an auto sampler for dilution purposes. The resulting water is suitable as a diluent to prepare standards for chromatographic calibration.

What is claimed is:

1. A method for electrolytically purifying an aqueous stream, adding a liquid sample stream containing an analyte ion to said purified aqueous stream, and detecting said analyte ion, said aqueous stream including at least one contaminant ion, said method comprising
   (a) flowing said aqueous stream through a purifying flow channel having an inlet and an outlet,
   (b) applying an electric field through said flowing aqueous stream in said purifying flow channel between first and second spaced electrodes of opposite charge, said first electrode being of opposite charge to said contaminant ion, and
   (c) removing said contaminant ion, but not ions of opposite charge to said contaminant ion, from said aqueous stream in said purifying flow channel to produce a purified aqueous stream which flows out said flow channel outlet while drawing said contaminant ion toward said first electrode,
   (d) adding a liquid sample to said purified aqueous stream exiting from said purifying flow channel, said liquid sample comprising at least a first analyte ion, said analyte ion being of the same charge, positive or negative, as said contaminant ion, and
   (e) detecting said analyte ion.

2. The method of claim 1 in which said aqueous stream comprises an eluent comprising and electrolyte comprising selected ions of one charge, positive or negative, said contaminant ion being of opposite charge to said selected ions.

3. The method of claim 1 in which flow-through ion exchange medium having exchangeable ions of the same charge as said contaminant ion is disposed in said purifying flow channel.

4. The method of claims 1 or 3 in which said second electrode is disposed proximal to said purifying flow channel outlet.

5. The method of claim 1 in which said first electrode is separated from said purifying flow channel by a barrier which permits the flow only of ions of the same charge as said contaminant ions.

6. The method of claim 5 in which said barrier blocks substantial bulk liquid flow.

7. The method of claim 5 in which said barrier is disposed along the purifying flow channel in contact with the eluent stream therein.

8. The method of claim 7 in which said barrier is disposed between said purifying flow channel inlet and outlet.

9. The method of claims 1 or 5 in which said first electrode is disposed in a first electrode chamber, said method further comprising flowing an aqueous solution through said electrode chamber to remove contaminants therefrom.

10. The method of claims 1 or 5 in which said first and second electrodes are disposed generally parallel to said purifying flow channel.

11. The method of claim 1 in which said first electrode is disposed proximate to said purifying flow channel inlet and said second electrode is disposed proximal to said purifying flow channel outlet.

12. The method of claim 1 in which said contaminant ion is carbonate or bicarbonate ion.

13. The method of claim 1 in which said liquid sample includes at least a second analyte ion, said method further comprising
(f) separating said first and second analyte ions of interest prior to detecting in step (e).

14. The method of claim 13 in which said separating is performed by chromatography.

15. A method for electrically purifying an aqueous stream, adding a liquid sample stream containing an analyte ion to said purified aqueous stream, said aqueous stream comprising an acid including an acid anion or a base including a base cation, said aqueous stream further including at least one contaminant ion of opposite charge to said acid anion for said acid aqueous stream and to said base cation for said base aqueous stream, said method comprising
(a) flowing said acid or base aqueous stream through a purifying flow channel having an inlet and an outlet,
(b) applying an electric field through said flowing aqueous stream in said purifying flow channel between first and second spaced electrodes of opposite charge, said first electrode being of opposite charge to said contaminant ion,
(c) removing said contaminant ion but not said acid anion or base cation from said aqueous stream in said purifying flow channel to produce a purified acid or base aqueous stream which flows out said flow channel outlet while drawing said contaminant ion toward said first electrode
(d) adding at least a first analyte ion to said purified acid or base aqueous stream exiting from said purifying flow channel, said first analyte ion being of the same charge, positive or negative, as said contaminant ion.

16. The method of claim 15 further comprising the steps of:
(e) flowing effluent from said chromatography medium through a suppressor chromatographic effluent flow channel separated by an ion exchange membrane from a suppressor regenerant flow channel, and
(f) flowing an aqueous liquid from said regenerant flow channel past said first electrode and removing aqueous solution in contact therewith.

17. The method of claim 15 in which said liquid sample comprises at least a second analyte ion, said method further comprising
(e) after step (c), separating said first and second analyte ions, and
(f) detecting said separated analyte ions.

18. The method of claim 17 in which said separation is performed by chromatography in a chromatography medium having the same charge, positive or negative, as said contaminant ion.

19. The method of claim 18 further comprising the steps of:
(g) flowing effluent from said chromatography medium through a suppressor chromatographic effluent flow channel separated by an ion exchange membrane from a suppressor regenerant flow channel, and
(h) flowing an aqueous liquid from said regenerant flow channel past said first electrode and removing aqueous solution in contact therewith.

20. The method of claim 15 in which said first electrode is separated from said purifying flow channel by a barrier which permits the flow only of ions of the same charge as said contaminant ions.

21. The method of claim 20 in which said first electrode is disposed in a first electrode chamber, said method further comprising flowing an aqueous solution through said electrode chamber to remove contaminants therefrom.

* * * * *

UNITED STATES PATENT AND TRADEMARK OFFICE
CERTIFICATE OF CORRECTION

PATENT NO. : 7,390,386 B2
APPLICATION NO. : 10/308865
DATED : June 24, 2008
INVENTOR(S) : Kannan Srinivasan and Nebojsa Avdalovic It is certified that error appears in the above-identified patent and that said Letters Patent is hereby corrected as shown below:

On the Title Page,
Item (73) Assignee should read: Dionex Corporation, Sunnyvale, CA (US)

Signed and Sealed this

Sixteenth Day of February, 2010

David J. Kappos
*Director of the United States Patent and Trademark Office*